United States Patent [19]

McCarthy, Jr.

[11] 4,029,703

[45] June 14, 1977

[54] N,N'-DI-SUBSTITUTED HALOPHENYLACETAMIDINES

[75] Inventor: James R. McCarthy, Jr., Midland, Mich.

[73] Assignee: The Dow Chemical Company, Midland, Mich.

[22] Filed: Feb. 11, 1976

[21] Appl. No.: 657,335

Related U.S. Application Data

[63] Continuation-in-part of Ser. No. 510,955, Oct. 2, 1974, abandoned, which is a continuation-in-part of Ser. No. 456,941, April 1, 1974, abandoned, which is a continuation of Ser. No. 279,651, Aug. 10, 1972, abandoned.

[52] U.S. Cl. .................... 260/564 R; 260/501.14; 424/316; 424/326
[51] Int. Cl.$^2$ ........................................ C07C 123/00
[58] Field of Search ................ 260/564 R, 501.14

[56] References Cited

OTHER PUBLICATIONS

Chemical Abstracts, vol. 59, col. 11522(g), (1963).
Chemical Abstracts, vol. 65, col. 2181(c), (1966).
Chemical Abstracts, vol. 64, col. 17, 499(f), (1966).

*Primary Examiner*—Gerald A. Schwartz
*Attorney, Agent, or Firm*—Maynard R. Johnson

[57] ABSTRACT

N,N'-Disubstituted halophenylacetamidine compounds such as N,N'-dimethyl-3,4-dichlorophenyl-acetamidine, and their pharmaceutically-acceptable salts are prepared by the reaction of a substituted phenylacetonitrile with an alkylamine and alkylammonium salt or alternatively, by reaction of the acetonitrile or corresponding N-alkylphenylacetamide with a trialkyloxonium fluoroborate followed by reaction with a primary alkylamine. The compounds have pharmacological activity as antidepressants and antianxiety or calming agents.

8 Claims, No Drawings

N,N'-DI-SUBSTITUTED HALOPHENYLACETAMIDINES

CROSS-REFERENCE TO RELATED APPLICATIONS

This is a continuation in-part of my copending application, Ser. No. 510,955, filed Oct. 2, 1974, now abandoned which was a continuation-in-part of application Ser. No. 456,941, filed Apr. 1, 1974, now abandoned, which in turn was a continuation of my application Ser. No. 279,651, filed Aug. 10, 1972, now abandoned.

BACKGROUND OF THE INVENTION

1. Description of the Prior Art

The substituted amidine compounds of the invention can be prepared by a modification of known methods. Typical methods which can be so modified include the reaction of a nitrile with a trialkyloxonium fluoroborate to prepare an N-alkyl nitrilium salt in a procedure similar to that of Meerwein et al., Ber. 89, 209 (1956), Borch, J. Org. Chem., 34, 627 (1969), and Weintraub et al. J. Org. Chem. 33, 1679 (1968). A number of N-monosubstituted and unsubstituted amidines are known. Craver et al. J. Pharm. Exptl. Therap. 99, 353 (1950); Netherlands Application 6,508,754, C.A. 65, 2181c (1966); U.S. Pat. Nos. 3,344,138, 3,417,122 and 3,334,137. Chlorobenzamidines are also known. Markwardt et al., Pharmazie, 1969, 24(7), 400-2, and European J. Biochem. 6; 502-6(1968).

2. SUMMARY OF THE INVENTION

This invention is directed to N,N'-disubstituted halophenylacetamidine compounds and is particularly directed to N,N'-disubstituted halophenyl-acetamidine compounds and their pharmaceutically-acceptable salts corresponding to the formula:

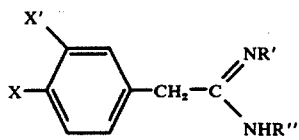

wherein X and X' represent halo or hydrogen, with the proviso that at least one of X and X' represents halo; and wherein R' and R" each independently represent loweralkyl of one to two to three carbon atoms. The compounds of the invention are generally crystalline solids at ordinary temperatures, and are variously soluble in conventional solvents such as water, alcohols, ether, benzene, chlorinated hydrocarbons and the like. The free base compounds are generally less soluble in water than the salts, particularly under alkaline conditions, while the pharmaceutically-acceptable salts are generally of moderate to good solubility in water and alcohols.

In the present specification and claims, the term "halo" is employed to designate one of the halogen moieties chloro or bromo.

The compounds of the invention are named as phenylacetamidines. For convenience, the compounds can be referred to generically as "substituted amidines". When R' and R" are different, the amidine moiety is subject to tautomerization, e.g.

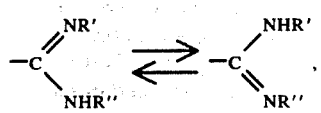

and the compound will generally be obtained as a mixture of the tautomers. Such mixtures of tautomers are useful as described herein, and for convenience will be named by naming only one tautomeric form. Compounds wherein R' and R" are identical are generally preferred. The term "pharmaceutically-acceptable salt" as herein employed refers to salts of a substituted amidine which are substantially non-toxic at dosages consistant with good pharmacological activity. Such pharmaceutically-acceptable salts include nontoxic acid addition salts with inorganic acids such as hydrochloric, hydrobromic, sulfuric or phosphoric acid, or with organic acids such as acetic, succinic, malic, maleic, tartaric or citric acid, or with organic sulfonic acids such as methanesulfonic or p-toluenesulfonic acid.

The substituted amidines of the invention have been found to be useful for administration to laboratory animals in the study of drug effects on the central nervous system, and have been found to be particularly useful as antidepressants and antianxiety or calmative agents. The compounds wherein X is chloro and X' is hydrogen or chloro have excellent antidepressant activity as well as calmative activity, and are preferred compounds.

The substituted amidines of the invention can be prepared by the reaction of the corresponding substituted phenylacetonitrile with a trialkyloxonium fluoroborate to prepare the corresponding N-alkyl substituted arylnitrilium fluoroborate salt; followed by the reaction of N-alkyl substituted arylnitrilium fluoroborate with a primary alkylamine. Alternatively, the substituted amidines of the invention can be prepared by the reaction of the corresponding N-alkyl phenylacetamide with a trialkyloxonium fluoroborate to prepare the corresponding N-alkyl phenylacetamidate salt; followed by the reaction of N-alkyl phenylacetamidate fluoroborate with a primary alkylamine.

These reactions are preferably carried out in the presence of an inert organic liquid such as methylene chloride or nitromethane.

In the preparation of the fluoroborate salt intermediates, the reaction proceeds when the acetonitrile or N-alkyl acetamide starting material and the trialkyloxonium fluoroborate are contacted and mixed in the presence of an anhydrous organic liquid reaction mixture. The mixing is carried out in dry reaction vessels under an inert gas blanket. The reaction proceeds at temperatures from about 0° C to about boiling under reflux, and is conveniently carried out at temperatures from about 25° C to about 50° C. The exact proportions of the reactants to be employed can be varied. However, it is convenient to employ from about 1 to about 3 molar proportions of the trialkyloxonium fluoroborate reactant for each molar proportion of nitrile or acetamide starting material. The reaction is generally complete within about 12 to about 72 hours depending on temperature employed. The intermediate salt can be separated by evaporation of the reaction medium, if desired, or it can be reacted with the primary alkylamine without separation. Preferably, the fluoroborate salt intermediate is not separated from the reaction mixture but is reacted directly with a primary alkylamine to prepare a substituted amidine product.

The reaction of the fluoroborate salt intermediate with the primary alkylamine proceeds when the reactants are contacted and mixed in the presence of an inert organic liquid reaction medium, such as nitromethane or methylene chloride. The reaction proceeds at temperatures of from about −70° C to about 30° C. The exact proportions of the reactants to be employed can be varied, however, the reaction consumes the reactants in equimolar proportions, and use of the reactants in such proportions or with an excess of the primary alkylamine reactant is preferred. The reaction is generally complete in about one to about 18 hours. The product can be separated by evaporation under reduced pressure followed by the addition of aqueous alkali to neutralize any remaining fluoroborate, followed by extraction with an organic solvent such as ethyl acetate. Alternatively, the product can be isolated directly as the fluoroborate salt by evaporation of the reaction medium and washing with water. The product can be purified by conventional procedures such as washing, recrystallization, extraction, or treatment on ion exchange resins. The free base product can also be purified by conversion to a pharmaceutically-acceptable salt and purification in the salt form. When the product is obtained as the fluoroborate salt, it can be conveniently neutralized to obtain the free base which can be purified or converted to a pharmaceutically-acceptable salt.

It will be immediately apparent that the foregoing procedure includes a number of disadvantages. It requires a two-step process; it requires an expensive and somewhat esoteric starting material, the trialkyloxonium fluoroborate salt; and the reaction requires anhydrous conditions and an inert gas blanket.

In addition, the yields of ultimate product have been found to be undesirably low - on the order of 30 to 40 percent. Accordingly, the invention also provides a novel method for preparing the amidines by a one-step procedure using relatively inexpensive reactants, which can produce the product in a desirable form in good yields and without requiring an inert gas to protect the reactants.

In the new procedure, the N,N'-disubstituted halophenylacetamidines are produced by reacting the corresponding halophenylacetonitrile directly with the corresponding primary amine and the corresponding primary ammonium ion,

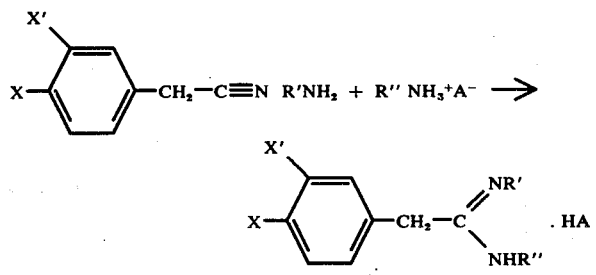

where, X, X', R' and R'' have the significance set out above, and A⁻ represents one anion. The structure of the amidine portion of the product in the above formula can also be written as

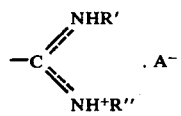

The reaction proceeds when the reactants are contacted and mixed, at a temperature in the range from about 140° C. to about 180° C. and under superatmospheric pressure. In a convenient procedure, the primary ammonium ion is conveniently supplied by using a primary ammonium salt, the anion of which (A in the above formula) is not detrimentally reactive with the other reactants. Suitable anions include inorganic anions, chloride, bromide, iodide, fluoride, sulfate, carbonate and organic anions such as toluenesulfonate, acetate, formate, etc. preferably a pharmaceutically-acceptable salt such as the chloride or bromide.

The proportions of reactants to be employed can be varied considerably; however, it is critical to employ an excess of the alkylamine. When a portion of alkylamine is employed as a salt, at least one molar proportion of the salt for each molar proportion of the nitrile starting material must be used so as to provide sufficient of the anion to obtain the product as a salt. In general, good results can be obtained by using, for each molar proportion of the nitrile, from about one to two to about ten molar proportions of alkylamine salt; and from about 20 to about 40 molar proportions of alkylamine (free base). A lower alkanol and excess alkylamine can also serve as a reaction medium, and the maximum proportions to be employed are limited by factors such as convenience of separating the product from the medium and increased reaction time and energy requirements as the excess of reaction medium is increased.

In a convenient procedure, about 20 to 40 molar proportions alkylamine, one to ten molar proportions of alkylamine salt, and about 20 to 100 molar proportions of a lower alkanol of 1 to 3 carbon atoms are employed per molar proportion of the nitrile. The materials are mixed together in a sealed reactor; such as a bomb, and heated at a temperature of about 130 to 180° C under a pressure of about 15 to 30 atmospheres until the reaction is substantially complete, generally from about 12 to about 20 hours. Substantially anhydrous conditions are preferably maintained during this procedure. The product can be separated by conventional procedures such as evaporation or distillation to remove excess medium and low boiling starting materials. It can be purified by conventional procedures, such as liquid-liquid extraction, washing, recrystallization and the like, and can be conveniently converted to the free base, purified in that form then converted to a pharmaceutically-acceptable salt for further purification.

The pharmaceutically-acceptable salts of the free base substituted amidines can be prepared by dissolving the free base in a minimal amount of alcohol, or ether or chloroform and adding an alcohol solution of an acid such as hydrochloric acid, hydrobromic acid, malic acid, maleic acid, p-toluenesulfonic acid, or succinic acid until precipitation of the corresponding salt is complete. The salt can further be purified by recrystallization or converted to the free base form.

The free base substituted amidine can be prepared by hydrolysis of the salt in aqueous base. The salt is mixed with a molar equivalent amount of sodium hydroxide in aqueous solution, excess aqueous sodium carbonate or the like, after which the free base can be separated by extraction with an organic solvent. The solvent can be removed by conventional methods such as evaporation or distillation. The product can be purified by conventional procedures such as washing or recrystallization.

DESCRIPTION OF THE PREFERRED EMBODIMENTS

The following examples illustrate the invention but are not to be construed as limiting the same.

EXAMPLE 1

21 Grams (0.1 mole) of triethyloxonium fluoroborate is dissolved in 150 milliliters of anhydrous methylene chloride and 18.6 grams (0.1 mole) of 3,4-dichlorophenylacetonitrile are added. All glassware employed has been previously dried at 125° C and held in a dessicator prior to use. The addition is carried out under dry nitrogen. The resulting mixture is heated with stirring for about 72 hours at a temperature of 35°–45° C. under dry nitrogen. The reaction mixture, containing the resulting N-ethyl 3,4-dichlorophenylacetonitrilium fluoroborate intermediate, is cooled to a temperature of −70° C in a Dry Ice-acetone bath, and 10 grams (0.22 mole) of dry monoethylamine is added. The resulting mixture is allowed to warm to room temperature (about 25° C) and is held for about 18 hours at room temperature with stirring. The mixture is concentrated by evaporation under reduced pressure, and the residue is taken up in a minimal amount of water, and made strongly basic by addition of excess aqueous 20 percent sodium hydroxide solution. The basic solution is extracted with an approximately equal volume of ethyl acetate and the ethyl acetate extract is dried over anhydrous magnesium sulfate. The ethyl acetate solution of the free base 2-(3,4-dichlorophenyl)-N,N'-diethylacetamidine product is saturated with dry hydrogen chloride gas whereupon the product precipitates in the form of the hydrochloride salt. The mixture is cooled to about 5° C, and filtered to obtain the hydrochloride salt product as a filter cake. A second crop of the 2-(3,4-dichlorophenyl)-N,N'-diethylacetamidine hydrochloride is obtained by evaporation of the filtrate, taking the residue up in acetone and filtering the acetone mixture. The combined product is recrystallized from a mixture of acetone and isopropanol and found to melt at a temperature of 230°–232° C. The product is found by elemental analysis to have carbon and hydrogen contents of 48.79 and 5.85 percent, respectively, as compared to the theoretical contents of 48.75 and 5.80 percent, respectively, calculated for the named structure. The structure of the named product is confirmed by infrared spectroscopy and nuclear magnetic resonance analysis.

In a similar procedure, the following are prepared: N,N'-dimethyl-2-(3,4-dibromophenyl)acetamidine hydrochloride, molecular weight 356.5; 2-(3-chloro-4-bromo-phenyl)-N,N'-diethylacetamidine hydrobromide, molecular weight 384.6; 2-(3,4-dibromophenyl)-N,N'dipropylacetamidine hydrobromide having a molecular weight of 457.

EXAMPLE 2

Using glass vessels dried at 125° C. before use, N-methyl-2-(4-chlorophenyl)acetamide (18.4 grams; 0.1 mole) is dispersed in a mixture of 150 milliliters of methylene chloride and triethyloxonium fluoroborate (19 grams; 0.1 mole). The reaction mixture is stirred at room temperature for 72 hours, then cooled in an acetone-Dry Ice bath while monomethylamine (10 grams; 0.33 mole) is added. The mixture is then stirred an additional 18 hours at room temperature. During the foregoing additions and mixing of reactants the mixture is maintained under a dry nitrogen blanket. The reaction mixture is then concentrated under vacuum and the residue is suspended in water, made strongly alkaline by addition of cold aqueous 20 percent sodium hydroxide, and extracted with ethyl acetate. The organic phase is separated and dried over anhydrous sodium sulfate. Excess dry gaseous hydrogen chloride is introduced into the mixture, and the resulting mixture is evaporated under reduced pressure, residual oil is taken up in methyl ethyl ketone, filtered and the filtrate evaporated. The product is obtained as a residue which is recrystallized from isopropanol. The 2-(4-chlorophenyl)-N,N'-dimethylacetamidine hydrochloride product is obtained in a yield of 4 grams; corresponding to a 17.1 percent yield based on the acetamide starting material. The product is found to melt at a temperature of 242.5°–243.5° C. Infrared and nuclear magnetic resonance analyses also confirm the named structure.

EXAMPLE 3

1.15 Mole of anhydrous methylamine is dissolved in 100 milliliters of anhydrous methanol and 0.05 mole of 2-(4-chlorophenyl)acetonitrile and 0.1 mole of methylamine hydrochloride are added. The resulting mixture is placed in a 300 milliliter bomb and heated for 15 hours at a temperature of 140° C. The pressure in the bomb during this reaction period is about 300 pounds per square inch gauge, about 21.4 atmospheres or 16,274 millimeters of mercury. The mixture is allowed to return to room temperature and pressure, then evaporated to dryness under reduced pressure. The residue is taken up in a mixture of 100 milliliters of chloroform and 100 milliliters of cold (0° C.) aqueous 10 percent sodium hydroxide. The organic layer is washed with three 100 milliliter portions of aqueous sodium chloride, dried over anhydrous sodium sulfate and evaporated to dryness in vacuo. The residue is taken up in a minimal amount of chloroform and an ether solution of hydrogen chloride is added whereupon the product precipitates in the form of the hydrochloride salt. The mixture is filtered to obtain the hydrochloride salt product as a filter cake, and dried in vacuo at room temperature to obtain the N,N'-dimethyl-2-(4-chlorophenyl)acetamidine hydrochloride product. Recrystallized from 2-propanol, mp 242.5°–243.5° C.

In a procedure similar to that of Examples 1–3 the following compounds of the invention are prepared:
  N,N'-Diethyl-2-(4-bromophenyl)acetamidine hydrochloride, melting at 173°–174° C. (recrystallized from isopropanol; having a molecular weight of 305.7;
  N,N'-Diisopropyl-2-(3-bromophenyl)acetamidine hydrochloride, having a molecular weight of 333.7;
  N,N'-Dimethyl-2-(3,4-dichlorophenyl)acetamidine hydrochloride, having a molecular weight of 267.6;
  N,N'-Di-n-propyl-2-(4-chlorophenyl)acetamidine hydrochloride, having a molecular weight of 289;
  N-Methyl-N'-ethyl-2-(3-chlorophenyl)acetamidine hydrochloride, tautomeric with N-ethyl-N'-methyl-2-(3-chlorophenyl)acetamidine hydrochloride, having a molecular weight of 247; is prepared by using equal parts of methylamine and ethylamine; in the procedure of Examples 1–3. The assymetrically substituted amidines are subject to tautomerism, and the product can be generally regarded as a mixture of the tautomeric forms.

The above compounds can also be prepared by the procedure of Example 3.

The substituted amidines of the invention have pharmacological activity in alleviating central nervous system depression and in alleviating symptoms of anxiety or nervous agitation. Thus, they can be administered to mammals by conventional routes such as orally or by intraperitoneal, intramuscular or intravenous injection to alleviate central nervous system depression or anxiety symptoms. A particular advantage of the compounds is that they exhibit little or no effect on the cardiovascular system and little or no anticholinergic activity at dosages consistent with good central nervous system activity. The compounds can be formulated with conventional pharmaceutical excipients to facilitate administration. As with most known pharmacologically active compounds, the substituted amidines vary somewhat in activity, and the amount of compound to be employed in a given situation will depend on such factors as the exact compound or pharmaceutically-acceptable salt employed, the route of administration, the animal treated, the formulation employed, etc.

In representative operations, the compound N,N'-dimethyl-2-(4-chlorophenyl)acetamidine hydrochloride is found to protect mice against central nervous system depression and ptosis resulting from intraperitoneal injection of reserpine at a dosage rate of 2.5 milligrams reserpine, per kilogram of body weight. The test compound is found to have an intraperitoneal $ED_{50}$ of 2 milligrams per kilogram, about one thirty-fifth its intraperitoneal acute $LD_{50}$ and about one two-hundred fifteenth its oral acute $LD_{50}$. When administered orally, the $ED_{50}$ is found to be 3 mg/kg for the same compound in the same procedure with mice, and 2 mg/kg in a similar procedure with rats. The compound is also found to potentiate hyperactivity, fighting and death resulting from subcutaneous administration of 20 mg/kg of yohimbine hydrochloride to mice aggregated in small cages. In these operations, the test compound is administered by intraperitoneal injection 30 minutes before the yohimbine challenge, and is found to potentiate lethality with an $ED_{50}$ of 15 mg/kg, indicating potent antidepressant action. In similar operations N,N'-diethyl-2-(3,4-dichlorophenyl)acetamidine hydrochloride is found to antagonize reserpine induced ptosis in mice with an intraperitoneal $ED_{50}$ of 3 mg/kg, and an oral $ED_{50}$ of 7 mg/kg. The test compound N,N'-diethyl-2-(4-bromophenyl)acetamidine hydrochloride is also found to inhibit reserpine induced ptosis.

In other operations, the test compound N,N'-dimethyl-2-(4-chlorophenyl)acetamidine hydrochloride is tested to evalute its effect on behavior of mice trained to avoid a mild electric shock administered through the cage floor by jumping to an insulated platform. Intraperitoneal administration of 10, 21.5 and 46 mg/kg of the test compound is found to have no significant effect on the learned shock-avoidance behavior. Calmative or anxiolytic activity is evaluated in a similar test in which two mice are combined in a small glass cage and subjected to mild electric shock through the cage floor. In this procedure, untreated mice exhibit aggression and fighting. The test compound N,N'-dimethyl-2(4-chlorophenyl)acetamidine hydrochloride is found to inhibit the electroshock-induced aggression with an intraperitoneal $ED_{50}$ of 43 mg/kg, when administered 30 minutes before the test.

What is claimed is:

1. A substituted amidine compound selected from the group consisting of halophenylacetamidine compounds corresponding to the formula

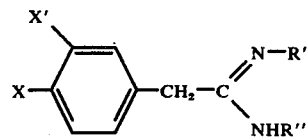

wherein X and X' independently represent halo or hydrogen, with the proviso that at least one of X and X' represents halo and R' and R" each independently represent loweralkyl; and the pharmaceutically-acceptable salts thereof.

2. A compound of claim 1 wherein R' and R" represent methyl.

3. A compound of claim 2 wherein X represents chloro and X' represents hydrogen.

4. A compound of claim 1 wherein the compound is N,N'-dimethyl-2-(4-chlorophenyl)acetamidine hydrochloride.

5. A compound of claim 1 wherein both X and X' are chloro.

6. A compound of claim 1 wherein the halo moiety is bromo.

7. A compound of claim 5 wherein R' and R" are both ethyl.

8. A compound of claim 7 wherein the compound is 2-(3,4-dichlorophenyl)-N,N'-diethylacetamidine hydrochloride.

* * * * *

UNITED STATES PATENT AND TRADEMARK OFFICE
CERTIFICATE OF CORRECTION

PATENT NO. : 4,029,703
DATED : June 14, 1977
INVENTOR(S) : James R. McCarthy, Jr.

It is certified that error appears in the above-identified patent and that said Letters Patent are hereby corrected as shown below:

Title page, Item [54], "N,N'-DI-SUBSTITUTED" should read
-- N,N'-DISUBSTITUTED --.

Column 1, first line of the title, "N,N'-DI-SUBSTITUTED"
should read                          -- N,N'-DISUBSTITUTED --.

Column 1, line 15, delete the numeral "1.".

Column 1, line 30, delete the numeral "2.".

Column 2, lines 49 and 50, "mixture" should read -- medium --.

Column 3, lines 47 thru 52, this portion of the reaction procedure should read:

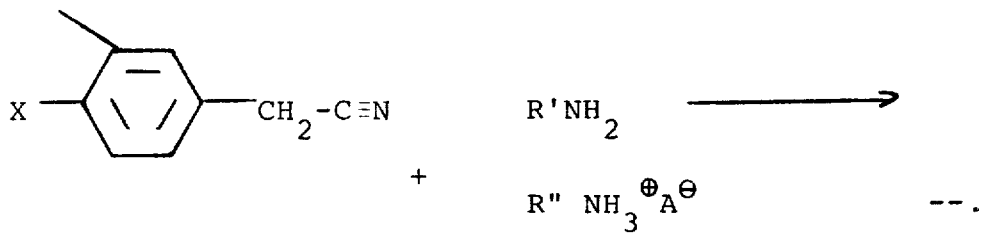

UNITED STATES PATENT AND TRADEMARK OFFICE
CERTIFICATE OF CORRECTION

PATENT NO.   : 4,029,703
DATED        : June 14, 1977
INVENTOR(S)  : James R. McCarthy, Jr.

It is certified that error appears in the above-identified patent and that said Letters Patent are hereby corrected as shown below:

Column 3, lines 64 thru 68, the amidine portion of the structure should read:

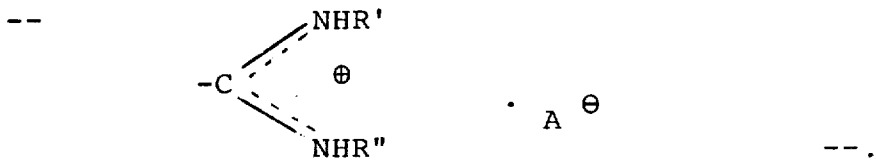

Column 8, line 5, "evalute" should read -- evaluate --.

Signed and Sealed this

Thirteenth Day of December 1977

[SEAL]

Attest:

RUTH C. MASON
*Attesting Officer*

LUTRELLE F. PARKER
*Acting Commissioner of Patents and Trademarks*